United States Patent [19]

Baker et al.

[11] 4,062,977
[45] Dec. 13, 1977

[54] SUBSTITUTED-N-(1,1-DISUBSTITUTED ETHYL)-α-(SUBSTITUTED PHENOXY)-α-ALKOXYACETAMIDES AND THEIR USE AS MITICIDES

[75] Inventors: Don R. Baker, Orinda; Francis H. Walker, Mill Valley, both of Calif.

[73] Assignee: Stauffer Chemical Company, Westport, Conn.

[21] Appl. No.: 705,504

[22] Filed: July 15, 1976

Related U.S. Application Data

[63] Continuation of Ser. No. 591,729, June 30, 1975, abandoned.

[51] Int. Cl.$^2$ .................... A01N 9/20; A01N 9/24; C07C 103/22
[52] U.S. Cl. .................... 424/324; 260/559 B
[58] Field of Search .................... 424/324; 260/559 B

[56] References Cited

U.S. PATENT DOCUMENTS

3,272,844   9/1966   Easton et al. .................... 260/559 B

*Primary Examiner*—V. D. Turner
*Attorney, Agent, or Firm*—M. Henry Heines; Michael J. Bradley

[57] ABSTRACT

Miticidally active compounds are described herein, which are defined by the following generic formula

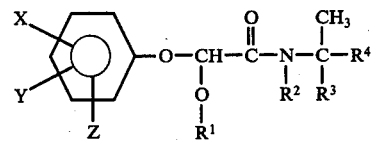

wherein X is selected from the group consisting of chlorine, fluorine, and trifluoromethyl; Y and Z are independently selected from the group consisting of hydrogen, chlorine, and methyl; $R^1$ is either methyl or ethyl; $R^2$ and $R^3$ are independently selected from the group consisting of hydrogen and methyl; and $R^4$ is either methyl or —C≡CH.

11 Claims, No Drawings

SUBSTITUTED-N-(1,1-DISUBSTITUTED ETHYL)-α-(SUBSTITUTED PHENOXY)-α-ALKOXYACETAMIDES AND THEIR USE AS MITICIDES

This is a continuation, of application Ser. No. 591,729, filed June 30, 1975, now abandoned.

BACKGROUND OF THE INVENTION

Various substituted amides, particularly N-substituted amides and substituted phenoxy amides, are known to be useful as insecticides, miticides, and herbicides. Typical insecticidal properties of such compounds are taught in U.S. Pat. No. 2,426,885 and its two continuations-in-part, U.S. Pat. Nos. 2,484,295 and 2,484,296. Herbicidal properties of such compounds are taught in U.S. Pat. Nos. 3,272,844, 3,439,018, and 3,564,607, and Belgian Pat. No. 739,714.

BRIEF DESCRIPTION OF THE INVENTION

This invention relates to a novel class of substituted amides and to their use as miticides when used in a miticidally effective amount. More specifically, this invention relates to N-substituted-N-(1,1-disubstituted ethyl)-α-(substituted phenoxy)-α-alkoxyacetamides having the formula

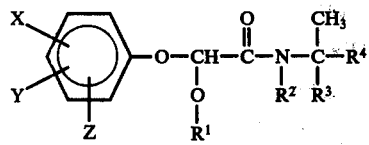

wherein X is selected from the group consisting of chlorine, fluorine, and trifluoromethyl; Y and Z are independently selected from the group consisting of hydrogen, chlorine, and methyl; $R^1$ is either methyl or ethyl; $R^2$ and $R^3$ are independently selected from the group consisting of hydrogen and methyl; and $R^4$ is either methyl or —C≡CH.

By "miticidally effective amount" is meant the amount of the herein disclosed miticidal compounds which when applied to the habitat of mites in any conventional manner will kill or substantially injure a significant portion of the population thereon.

DETAILED DESCRIPTION OF THE INVENTION

The compounds of the present invention can be prepared by the following general method:

Reaction No. 1

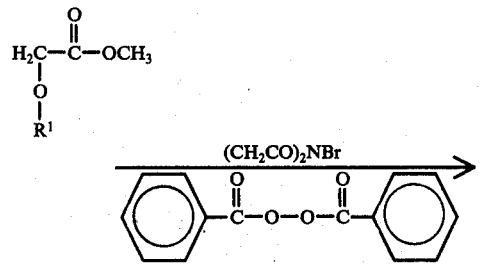

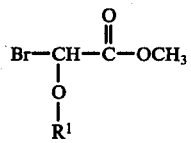

Generally, a mole amount of the ester, a slight mole excess of the succinimide, and a few crystals of the peroxide are mixed in carbon tetrachloride and heated to reflux for an hour. The mixture is then cooled and filtered and the filtrate is evaporated to leave an oil.

Reaction No. 2

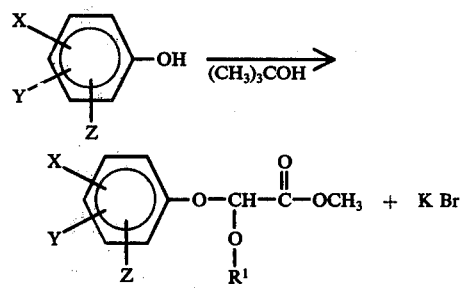

The potassium t-butoxide is first dissolved in t-butyl alcohol, followed by addition of the phenol and finally the ester, the latter two reactants approximately equal in molar quantity to the butoxide. In the ensuing exothermic reaction, the potassium bromide separates from the mixture which is subsequently poured into water and extracted with chloroform.

Alternatively, the following reaction may be used:

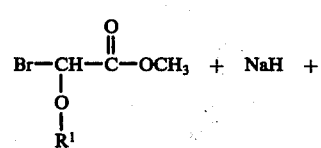

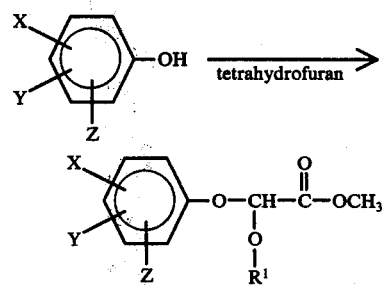

A solution of the phenol in tetrahydrofuran is added to a solution of sodium hydride and stirred. A solution of the ester is then added and the mixture is heated to reflux and cooled. The sodium bromide is removed by filtration and the filtrate is evaporated to leave an oil.

Following either of these reactions, the ester is converted to an acid which is subsequently extracted, washed, and dried. The solvent is removed in a vacuum and the acid is recrystallized from cyclohexane. The acid is then dissolved in a suitable solvent, converted to the sodium salt, and then recovered from the solvent.

Reaction No. 3

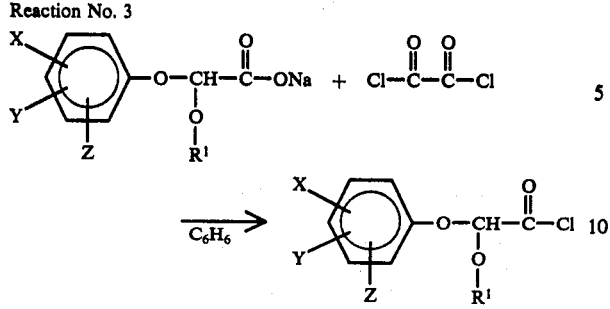

This reaction is conducted according to the method of R. Adams and L. H. Ulich, J. Am. Chem. Soc., 42, 599 (1920). The product mixture is then filtered and the filtrate evaporated to leave a liquid.

Reaction No. 4

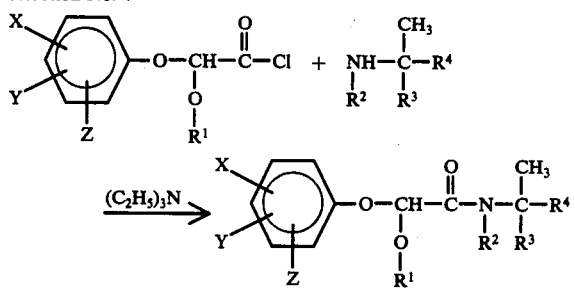

The acid chloride, dissolved in a suitable solvent, is added to a solution of both the disubstituted amine and the triethylamine. The mixture is subsequently washed and dried, and the solvent is evaporated to leave the product oil.

The examples shown herein are illustrative of the method of preparation of the compounds of the invention.

EXAMPLE I

N-dimethylpropynyl-α-methoxy-α-(3,5-dichlorophenoxy)acetamide.

(Compound No. 1 in Table I below)

A mixture of 20.0 g (0.19 mole) methyl 2-methoxyacetate, 34.6 g (0.20 mole) N-bromosuccinimide and a few crystals of benzoyl peroxide in 200 ml carbon tetrachloride was heated to reflux. After an initial vigorous reaction, the mixture was heated for 1 hour, cooled, and filtered. The filtrate was evaporated at 15 mm pressure on a rotary evaporator to leave 34.0 g (98% yield) of an oil, $n_D^{30}$ 1.4694, identified by NMR analysis as methyl-α-bromo-α-methoxyacetate.

Potassium t-butoxide, 24.7 g (0.22 mole), was dissolved in 250 ml t-butyl alcohol. The mixture was stirred for 15 minutes at room temperature. 3.6 g (0.22 mole) of 3,5-dichlorophenol was then added, followed by 40.4 g (0.22 mole) of methyl 2-bromo-2-methoxyacetate. The addition occurred at 35°–40° C. The reaction was exothermic with separation of potassium bromide. After 3 hours of stirring with no external heating, the mixture was poured into 600 ml water and the resulting mixture was extracted with two 150 ml portions of chloroform. The extracts were combined and washed with three 150 ml portions of saturated sodium chloride solution. The solution was then dried over magnesium sulfate and evaporated to leave 53.8 g of a liquid, $n_D^{30}$ 1.5244, identified by infrared spectroscopy as methyl-α-(3,5-dichlorophenoxy)-α-methoxyacetate.

A solution of 53.8 g (0.20 mole) of the above liquid product in 50 ml ethanol was added slowly to a solution of 13.9 g (0.21 mole) of 85% KOH in 200 ml ethanol. The mixture was heated at 45° C for one-half hour, then cooled to room temperature and poured into 300 ml of water. The pH of the resulting mixture was adjusted to 2 with dilute HCl. An oil separated which was removed by two 150 ml extractions with chloroform. The chloroform extracts were combined, washed with three 150 ml portions of water and dried over magnesium sulfate. Removal of the solvent in vacuum left a solid, 40.9 g (81% crude yield) which was recrystallized from cyclohexane to give 3,5-dichlorophenoxymethoxyacetic acid, m.p. 79°–82° C. 25.1 g (0.10 mole) of the acid was dissolved in 75 ml anhydrous methanol. 28.6 g (0.13 mole) of a 25% solution of sodium methoxide in methanol was then added. After one-half hour, the solution was evaporated to give 26.1 g of sodium α-(3,5-dichlorophenoxy)-α-methoxyacetate.

According to the method of Adams and Ulich, supra, 14.0 g (0.11 mole) of oxalyl chloride and 25 ml dry benzene were placed in a 300 ml flask fitted with a thermometer, a stirrer, and a reflux condenser. A 125 ml Erhlenmeyer flask containing 25.7 g (0.10 mole) of sodium 3,5-dichlorophenoxymethoxyacetate was attached to the flask with Gooch tubing. While the oxalyl chloride solution was stirred, the sodium salt was added in portions by tipping up the flask. After all the sodium salt had been added, the mixture was heated at 45° C for two hours and cooled. The mixture was filtered and the filtrate was evaporated to leave a liquid, 25.2 g (98.4% yield), identified by infrared spectroscopy as α-(3,5-dichlorophenoxy)-α-methoxyacetyl chloride.

A solution of 4.3 g (0.052 mole) dimethylpropargylamine and 5.3 g (0.052 mole) triethylamine in 50 ml benzene was cooled to 10° C in an ice bath and a solution of 12.6 g (0.047 mole) 3,5-dichlorophenoxymethoxyacetyl chloride in 25 ml benzene was added slowly with stirring. After addition was complete, the cold bath was removed and the mixture was allowed to come to room temperature. The mixture was then washed, first with 100 ml water, followed by two 100 ml portions of 5% sodium carbonate solution. The mixture was then dried over magnesium sulfate. Evaporation of the solvent left 4.6 g (31% yield) of an oil, $n_D^{30}$ 1.5291, identified by NMR spectroscopy as N-dimethylpropynyl-α-methoxy-α-(3,5-dichlorophenoxy)acetamide.

EXAMPLE II

N-dimethylpropynyl-α-methoxy-α-(3,4,5-trichlorophenoxy) acetamide. (Compound No. 2 in Table I below)

A solution of 50 g (0.25 mole) of 3,4,5-trichlorophenol in 75 ml tetrahydrofuran was added dropwise to a mixture of 6.0 g (0.25 mole) of sodium hydride in 75 ml tetrahydrofuran, with stirring under an argon atmosphere. At the conclusion of the phenol addition, the mixture was stirred for an additional half hour. A solution of 45.8 g (0.25 mole) of methyl 2-bromo-2-methoxyacetate (prepared according to the procedure of Example I) in 30 ml tetrahydrofuran was added to the above-mentioned sodium hydride-trichlorophenol mixture over a period of 15 minutes with stirring. The temperature rose to 46° C over this period. When the addition was complete, the mixture was heated at reflux for one-half hour, cooled, and filtered. The filtrate was evaporated to leave 44.4 g (59.3% yield) of an oil, $n_D^{30}$ 1.5428, identified by infrared spectroscopy as methyl-α-(3,4,5-trichlorophenoxy)-α-methoxyacetate.

A solution of 35.2 g (0.12 mole) methyl-α-(3,4,5-trichlorophenoxy)-α-methoxyacetate in 50 ml ethanol was added slowly to a solution of 9.2 g (0.14 mole) 85% KOH in 150 ml 2B ethanol. The mixture was heated at 45° C for one-half hour, then cooled to room temperature and poured into 300 ml H₂O. The pH of the resulting mixture was adjusted to 2 with dilute HCl. An oil separated which was removed by two 150 ml extractions with chloroform. The chloroform extracts were combined, washed with three 150 ml portions of water, and dried over magnesium sulfate. Removal of the solvent in vacuum left 22.9 g (66.8% crude yield) of a solid which was recrystallized from cyclohexane to give α-(3,4,5-trichlorophenoxy)-α-methoxyacetic acid, m.p. 101°–104° C, characterized by infrared spectroscopy. 20.0 g (0.07 mole) of the acid dissolved in 25 ml tetrahydrofuran was added dropwise to 1.9 g (0.08 mole) sodium hydride in 75 ml tetrahydrofuran. One half hour after addition was complete, the solution was evaporated to leave the sodium salt. This was added by portions to a solution of 8.9 g (0.07 mole) oxalyl chloride in 150 ml benzene to give 15.7 g (73.8% yield) of an oil, α-(3,4,5-trichlorophenoxy)-α-methoxyacetyl chloride. Due to its air sensitivity, 5.2 g (0.02 mole) of this compound was immediately dissolved in 25 ml benzene and added slowly to a solution of 1.7 g (0.02 mole) dimethylpropargylamine and 2.1 g (0.02 mole) triethylamine in 100 ml benzene, with stirring while the solution was being cooled to 10° C in an ice bath. After addition was complete the cold bath was removed and the mixture was allowed to come to room temperature. The mixture was then washed first with 100 ml water, followed by two 100 ml portions of 5% sodium carbonate solution. The organic phase was dried over magnesium sulfate, and the solvent was evaporated to give 5.4 g (77.1% yield) of a solid, which was recrystallized from hexane and characterized by infrared and NMR spectroscopy as in N-dimethylpropynyl-α-methoxy-α-(3,4,5-trichlorophenoxy)acetamide, m.p. 76°–80° C.

Other compounds, such as those included in the following table, can be prepared in a manner analogous to that shown in the examples above, starting with the appropriate materials. The compounds in the table are representative of those embodied in the present invention. Compound numbers have been assigned to them for purposes of identification throughout the balance of this specification.

TABLE I

| COMPOUND NUMBER | COMPOUND |
|---|---|
| 1 | 3,5-dichlorophenyl-O-CH(OCH₃)-C(O)-NH-C(CH₃)₂-C≡CH |
| 2 | 3,4,5-trichlorophenyl-O-CH(OCH₃)-C(O)-NH-C(CH₃)₂-C≡CH |
| 3 | 3,5-dichlorophenyl-O-CH(OC₂H₅)-C(O)-NH-C(CH₃)₂-C≡CH |
| 4 | 3,4,5-trichlorophenyl-O-CH(OCH₃)-C(O)-NH-C(CH₃)₃ |
| 5 | 3-fluoro-5-chlorophenyl-O-CH(OC₂H₅)-C(O)-N(CH₃)-CH(CH₃)₂ |
| 6 | 3-CF₃-phenyl-O-CH(OC₃H₅)-C(O)-NH-C(CH₃)₃ |
| 7 | 3-Cl-4,5-di-CH₃-phenyl-O-CH(OC₂H₅)-C(O)-NH-C(CH₃)₂-C≡CH |
| 8 | 3-Cl-5-CF₃-phenyl-O-CH(OCH₃)-C(O)-NH-C(CH₃)₂-C≡CH |
| 9 | 2,3,5-trichlorophenyl-O-CH(OCH₃)-C(O)-N(CH₃)-CH(CH₃)-C≡CH |

Miticidal activity of selected compounds from the above Table I on the two-spotted mite [Tetranychus urticae (Koch)] was evaluated as follows:

I. Plant Dip Assay

Pinto bean plants (*Phaseolus sp.*), approximately 10 cm tall, are transplanted into sandy loam soil in 3-inch clay pots and thoroughly infested with two-spotted mites of mixed ages and sexes. Twenty-four hours later the infested plants are inverted and dipped for 2-3 seconds in 50—50 acetone-water solutions of the test chemicals. Treated plants are held in the greenhouse, and seven days later mortality is determined for both the adult mites and the nymphs hatching from eggs which were on the plants at the time of treatment. Test concentrations range from 0.05% down to that at which 50% mortality occurs.

II. Systemic Assay

Test chemicals are dissolved in acetone and aliquots are diluted in 200 cc of water in glass bottles. Two pinto bean plants (*Phaseolus sp.*), with expanded primary leaves, are supported in each bottle by cotton plugs, so that their roots and stems are immersed in the treated water. The plants are then infested with 75-100 two-spotted mites of various ages and sexes. One week later the mortality of the adult mites and nymphs is recorded. Test concentrations range from 10 ppm down to that at which 50% mortality occurs.

The results of the above test procedures, indicating the effective concentration at which 50% mortality was achieved, are listed in Table II.

TABLE II

| Effective Concentrations on Two-Spotted Mite [Tetranychus urticae (Koch)] | | | |
|---|---|---|---|
| COMPOUND NUMBER | PE (%) | Eggs (%) | SYS (%) |
| 1 | .005 | .01 | 10 |
| 2 | .003 | .008 | >10 |
| 3 | .005 | .005 | >10 |
| 4 | .05 | .05 | — |

PE = Post-embryonic
SYS = Systemic
>> Greater than

Neither the examples nor the tables above are intended to limit the invention in any manner.

The compounds of this invention are generally embodied in a form suitable for convenient application. For example, the compounds can be embodied in miticidal compositions in the form of emulsions, suspensions, solutions, dusts, and aerosol sprays. In addition to the active compounds, such compositions generally contain the adjuvants which are normally found in miticide preparations. One such composition can contain either a single miticidally active compound or a combination of miticidally active compounds. The miticide compositions of this invention can contain as adjuvants organic solvents such as sesame oil, xylene, or heavy petroleum; water; emulsifying agents; surface active agents; talc; pyrophyllite; diatomite; gypsum; clays; or propellants such as dichlorodifluoromethane; or a combination of these. If desired, however, the active compounds can be applied directly to feedstuffs, seeds, or other such matter upon which the pests feed. When applied in such a manner, it will be advantageous to use a compound which is not volatile. In connection with the activity of the presently disclosed miticidal compounds, it should be fully understood that the compounds need not be active as such. The purposes of this invention will be fully served by a compound which is rendered active by an external influence such as light, or by some physiological action which the compound induces when it is ingested into the body of the pest.

The precise manner in which the miticidal compounds of this invention should be used in any particular instance will be readily apparent to a person skilled in the art. The concentration of the active miticide in a typical composition can vary within rather wide limits. Ordinarily, the miticide will comprise not more than about 15.0% by weight of the composition. The preferred range of concentration of the miticide is about 0.1 to about 1.0% by weight.

We claim:

1. A method of controlling mites comprising applying to said mites a miticidally effective amount of a compound having the formula

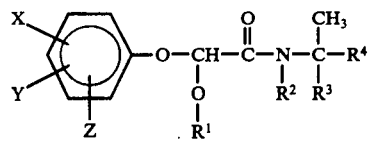

wherein X is selected from the group consisting of chlorine, flourine, and trifluoromethyl; Y and Z are independently selected from the group consisting of hydrogen, chloride, and methyl; $R^1$ is either methyl or ethyl; $R^2$ and $R^3$ are independently selected from the group consisting of hydrogen and methyl; and $R^4$ is either methyl or —C≡CH.

2. A method according to claim 1 in which X is chlorine.

3. A method according to claim 1 in which $R^4$ is —C≡CH.

4. A method according to claim 3 in which X is 3-chloro, Y is 5-chloro, Z is hydrogen, $R^1$ is methyl, $R^2$ is hydrogen, and $R^3$ is methyl.

5. A method according to claim 3 in which X is 3-chloro, Y is 4-chloro, Z is 5-chloro, $R^1$ is methyl, $R^2$ is hydrogen, and $R^3$ is methyl.

6. A method according to claim 3 in which X is 3-chloro, Y is 5-chloro, Z is hydrogen, $R^1$ is ethyl, $R^2$ is hydrogen, and $R^3$ is methyl.

7. A method according to claim 1 in which $R^4$ is methyl.

8. A method according to claim 7 in which X is 3-chloro, Y is 4-chloro, Z is 5-chloro, $R^1$ is methyl, $R^2$ is hydrogen, and $R^3$ is methyl.

9. A compound having the formula

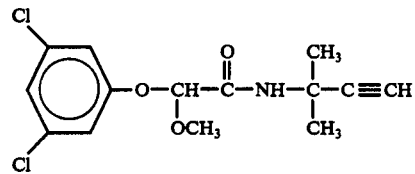

10. A compound having the formula

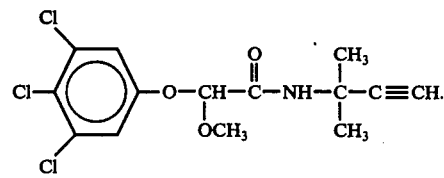

11. A compound having the formula

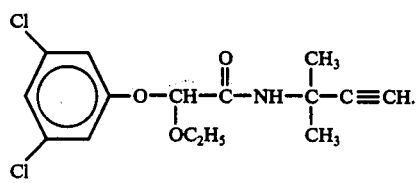

* * * * *